United States Patent [19]
Schwab

[11] Patent Number: 4,506,994
[45] Date of Patent: Mar. 26, 1985

[54] DEW POINT MEASUREMENT AND TIME TREND ANALYSIS

[75] Inventor: Carl E. Schwab, Huntington Station, N.Y.

[73] Assignee: General Signal Corporation, Stamford, Conn.

[21] Appl. No.: 419,884

[22] Filed: Sep. 20, 1982

[51] Int. Cl.³ ............................................. G01N 25/66
[52] U.S. Cl. .................................... 374/28; 73/336.5; 250/574; 356/37; 374/163
[58] Field of Search ...................... 374/28; 73/73, 335, 73/336.5; 356/37; 340/637, 601, 602

[56] References Cited

U.S. PATENT DOCUMENTS

| | | | |
|---|---|---|---|
| 1,945,660 | 2/1934 | Scott | 73/29 |
| 2,654,242 | 10/1953 | Fallgatter et al. | 73/29 |
| 2,715,836 | 8/1955 | Brady | 374/28 X |
| 2,829,363 | 4/1958 | Obermaier et al. | 356/37 X |
| 3,177,716 | 4/1965 | Warman | 73/335 |
| 3,406,387 | 10/1965 | Werme | 340/637 X |
| 3,552,187 | 1/1971 | Groninger | 73/336.5 X |
| 3,636,768 | 1/1972 | Tinet et al. | 73/336.5 |
| 3,850,524 | 11/1974 | Kanter | 356/37 |
| 3,926,052 | 12/1975 | Bechtel | 73/336.5 |
| 4,269,060 | 5/1981 | Kethley | 73/335 X |
| 4,278,970 | 7/1981 | Streczyn | 374/185 X |
| 4,319,485 | 3/1982 | Terada et al. | 73/336.5 X |

FOREIGN PATENT DOCUMENTS 0813209 3/1981 U.S.S.R. .............................. 340/602

OTHER PUBLICATIONS

"Tired of Just Reading Results? Let Your Investment Do the Talking, by V. B. Tandon, pp. 160–163 of Design Engineering, (El. Design 24), 11/78.
Class 356–37, Search Card Definition, 11-9-64.

*Primary Examiner*—Daniel M. Yasich
*Attorney, Agent, or Firm*—Pollock, Vande Sande and Priddy

[57] ABSTRACT

A method and apparatus for determining the dew point or dew point depression which is arranged for unattended operation and is extremely accurate in the vicinity of very small dew point depressions. In addition to measuring present dew point depression, historical records are maintained and the device is arranged to perform a time trend analysis so as to provide for short term future prediction. Output is provided via a voice synthesizer and a radio. Dew point depression is computed by determining the adiabatic change in volume required to produce condensation. The change in volume is produced by rapidly expanding a test chamber. The measurement cycle concludes with a compression step to raise chamber temperature to at least freezing.

15 Claims, 6 Drawing Figures

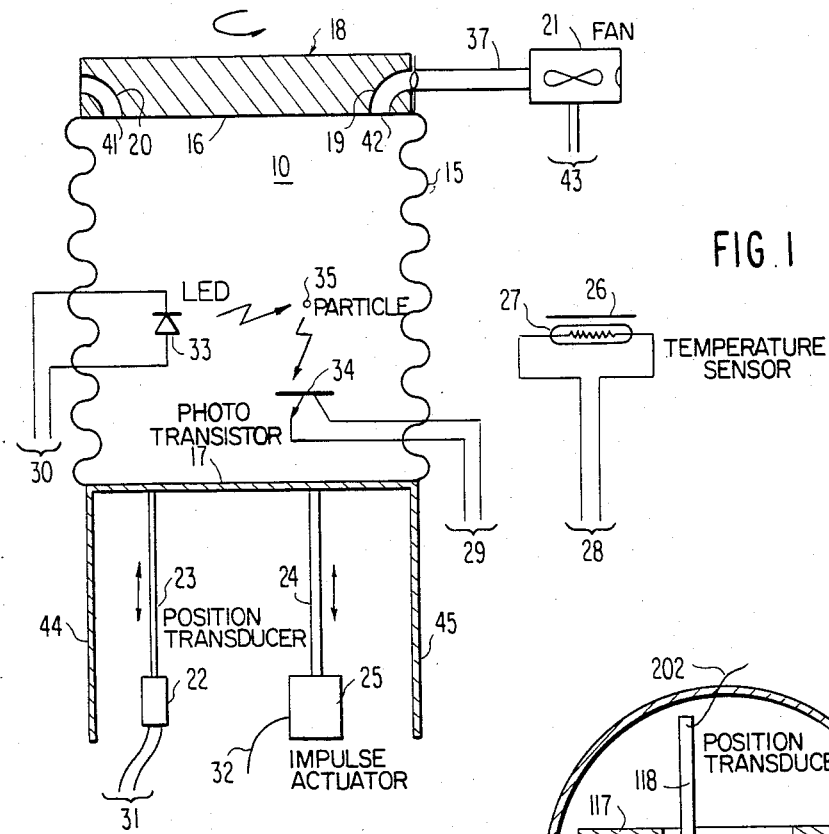
FIG. 1
FIG. 2
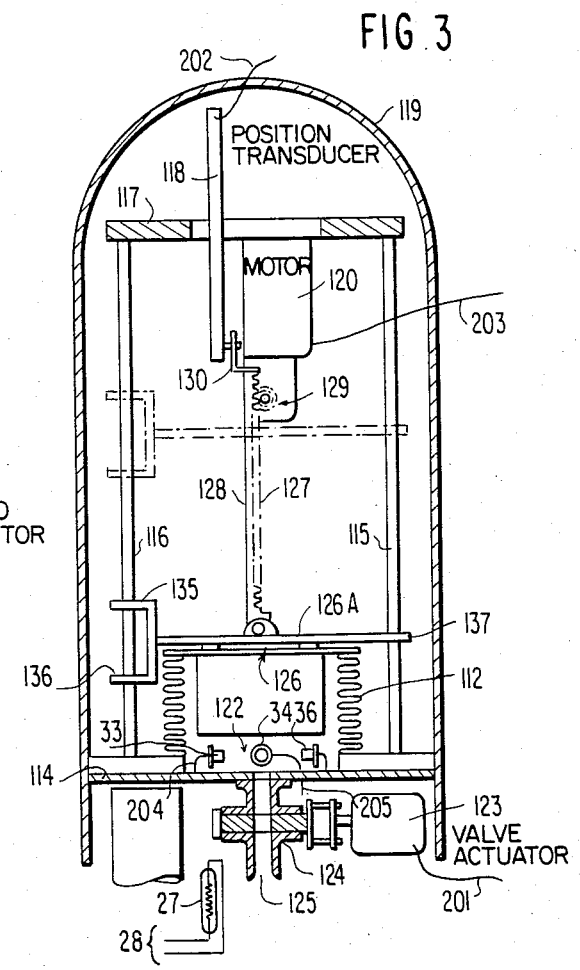
FIG. 3

DEW POINT MEASUREMENT AND TIME TREND ANALYSIS

DESCRIPTION

1. Field of the Invention

The invention relates to a method and apparatus for accurately determining dew point depression, especially such a device which is capable of use under high relative humidity conditions and which is particularly applicable to airport operations.

2. Background Art

For a number of reasons, the use of secondary airports is expected to increase, for these purposes a secondary airport is one that does not qualify for a full time weather observer. Accordingly, a great deal of interest has been expressed in using machine measured parameters to determine visibility conditions to assist in deciding on various suitable alternate fields. One proposed machine, WAVE (proposed by the FAA), measures wind, altimeter setting, temperature and dew point and uses a voice encoding arrangement to report this information directly to the pilots of approaching aircraft on request.

Two major concerns to the pilot of an approaching aircraft relative to dew point are possible icing conditions that can affect aerodynamics and engine performance of the aircraft, and fogging that may limit visibility by the time he can reach the field. Based on these concerns, three different desirable characteristics can be identified:

First, the machine should function accurately in and around freezing temperatures.

Second, it should have the most accuracy where the dew point is only a few degrees below ambient, indicating high humidity, where only a few degrees drop in ambient temperature can produce ice, fog, precipitation, or all three. It is in this area that most current devices are weak.

Third, it is vital to know what the trend in ambient temperature is—is it rising, falling, and what is the rate of change?

Typical prior art devices make use of some physical phenomena that occurs because of moisture content of air. Some characteristics that have been used include:

1. Mechanical dimension change of some sensing element,
2. Resistance change to electrical current flow as a function of moisture content,
3. EMF generating effects,
4. Temperature differences as a result of evaporation rate,
5. Cooling of an air sample and detection of dew point.

The use of these phenomena, especially as implemented in prior art devices, are plagued by slow response, inaccuracy at high humidity, excessive maintenance, inability to operate below freezing temperatures, or some combination of the preceding difficulties. In spite of these difficulties, these devices have been useful for general meteorological data gathering where readings are taken over many days and months and where it is important to know the relative humidity has increased 15% over the past 24 hours, even though the device cannot define whether the change has been from 40% to 55% humidity or 45% to 60% humidity.

This is exemplified by specifications which call for relative humidity measurement from, say 10% to 95%, from $-20°$ C. to $+40°$ C., or a dew point measurement between the temperatures of $-30°$ C. to $+30°$ C. with no special emphasis on accuracy at high humidities.

As specified above, what would be more valuable for aviation purposes is a dew point measurement that has greatest accuracy for small depressions and functions for example from $-20°$ C. to $+40°$ C. ambient temperature. Outside this ambient temperature range, the probability of visibility impairments and icing conditions is nil. Also of significance, and missing from the prior art, are devices to foretell what visibility/icing conditions will exist in the short term (e.g. 1 hour) so that a pilot can make vital decisions.

Therefore, it is an object of the invention to provide a device for measuring dew point or dew point depression which is capable of relatively rapid measurement. It is another object of the present invention to effect this rapid measurement with high accuracy, especially near freezing temperatures. It is a further object of the invention to provide such a device which has rapid and accurate characteristics as aforesaid, and which is also capable of operating below freezing temperatures. It is still another object of the invention to provide a method and apparatus which meets the foregoing objects and which is capable of automatic, unattended operation. It is still another object of the invention to provide a device which can integrate present dew point or dew point measurements with historical measurements and derive a dew point or a dew point depression trend analysis so as to allow short term future predictions. It is still another object of the invention to provide a device as aforesaid which is readily capable of being interfaced with audio synthesizing equipment so as to automatically radio, either constantly or on demand, dew point or dew point depression information to pilots of approaching aircraft.

SUMMARY OF THE INVENTION

These and other objects of the invention are met by a method and apparatus for measuring dew point or dew point depression.

In accordance with the apparatus aspects of the invention, a measuring device is provided which includes a valved test chamber of controllable volume. Apparatus is provided for introducing air into the test chamber at near ambient temperature and pressure conditions; this apparatus includes a controllable valve. An aspirating technique is used to fill the chamber, and this may include either a slowly rotating fan and/or suction techniques. At some point, the controllable volume is sealed by operating the valve. Thereafter, the volume of the test chamber is abruptly expanded. This closely approximates adiabatic expansion. Means are provided for sensing the formation of water or ice particles. Preferably, this sensing employs a light source and a light responsive device arranged so that light emitted by the light source will be reflected into the photo responsive device by water or ice particles; the devices are geometrically arranged so that there is no direct path from the light source to the photo responsive device. A transducer measures the volume of the test chamber, as it varies, and the volume change of the test chamber on the formation of water or ice particles is noted. With this information, the dew point or dew point depression can be calculated. The apparatus may continuously cycle by thereafter decreasing the volume of the test chamber or it can be operated at discrete times. Decreasing the volume of the test chamber with the valve closed causes local heating and prevents formation of large ice particles which could interfere with operation. During the compression cycle, the valve is again opened and the air previously sampled is exhausted to the atmosphere. Thereafter, the cycle can begin again by charging the test chamber with new air.

In one embodiment of the device, the test chamber volume has a lower limit which is fixed. After the test chamber is charged to (near) atmospheric conditions, the valve is closed and the chamber is abruptly expanded. This embodiment of the invention implements the aspirating technique with a slowly rotating fan.

In another form of the invention, however, the test chamber volume can be decreased below a reference volume which is filled with atmospheric air; in this embodiment of the invention the aspirating technique is suction. Actually, in this embodiment of the invention, the reference volume need not be constant since it is only necessary to measure the change in volume of the test chamber which is required to produce, from atmospheric conditions, the formation of water or ice particles. Recording the transducer output (related to volume) at two points (ambient and later, on formation of water or ice) in the cycle provides a measurement of change in volume over this range.

Accordingly, in one aspect the invention comprises a device for measuring dew point comprising:

a test chamber with controllable volume, first means for introducing air into said chamber at or near ambient temperature and pressure conditions, second means for opening and closing said test chamber to ambient atmospheric conditions, third means for abruptly expanding said test chamber in volume after said test chamber is sealed by said second means, fourth means for detecting water or ice particles in said test chamber, fifth means for recording test chamber volume at the time said fourth means detects formation of ice or water particles, and sixth means for computing dew point based on ambient temperature and said test chamber volume variation required to produce said water or ice particles.

Correspondingly, the method of the invention comprises a method of accurately measuring dew point under high relative humidity conditions comprising the steps of:

providing a valved test chamber of controllable volume, introducing air into said chamber at nearly ambient temperature and pressure conditions, sealing the chamber, abruptly increasing the volume of said chamber, and determining dew point by noting the volume variation of said chamber required to produce ice or water particles.

Preferably, the control of the various components of the device are coordinated by a microprocessor which controls the compression and expansion of the test chamber, operation of the valve, and records condition of the volume measuring transducer at appropriate points in time. The same microprocessor is programmed so as to compute from the various input data, the required dew point or dew point depression. In addition, the presence of the microprocessor allows present dew point or dew point depression data to be integrated with historical dew point or dew point depression data so as to develop a trend analysis, allowing short term prediction of future dew point or dew point depression.

A further advantage of the use of the microprocessor is readily interfacing the components of the invention thus far described with conventional voice synthesis and radio equipment. This allows data corresponding to dew point or dew point depression along with the results of the trend analysis to be converted to audio form, via the conventional voice synthesizer, and then inputting the information in audio form to the radio for transmission to pilots of approaching aircraft, either continuously, or on demand.

BRIEF DESCRIPTION OF THE DRAWINGS

The present invention will now be described so as to enable those skilled in the art to make and use the same, in the following portions of the specification when taken in conjunction with the attached drawings in which like reference characters identify identical apparatus and in which:

FIGS. 1 and 2 illustrate the interrelationship of functional components of one embodiment of the invention;

FIG. 3 is a cross-section of a different embodiment of the invention;

DETAILED DESCRIPTION OF PREFERRED EMBODIMENTS

Figure 4:
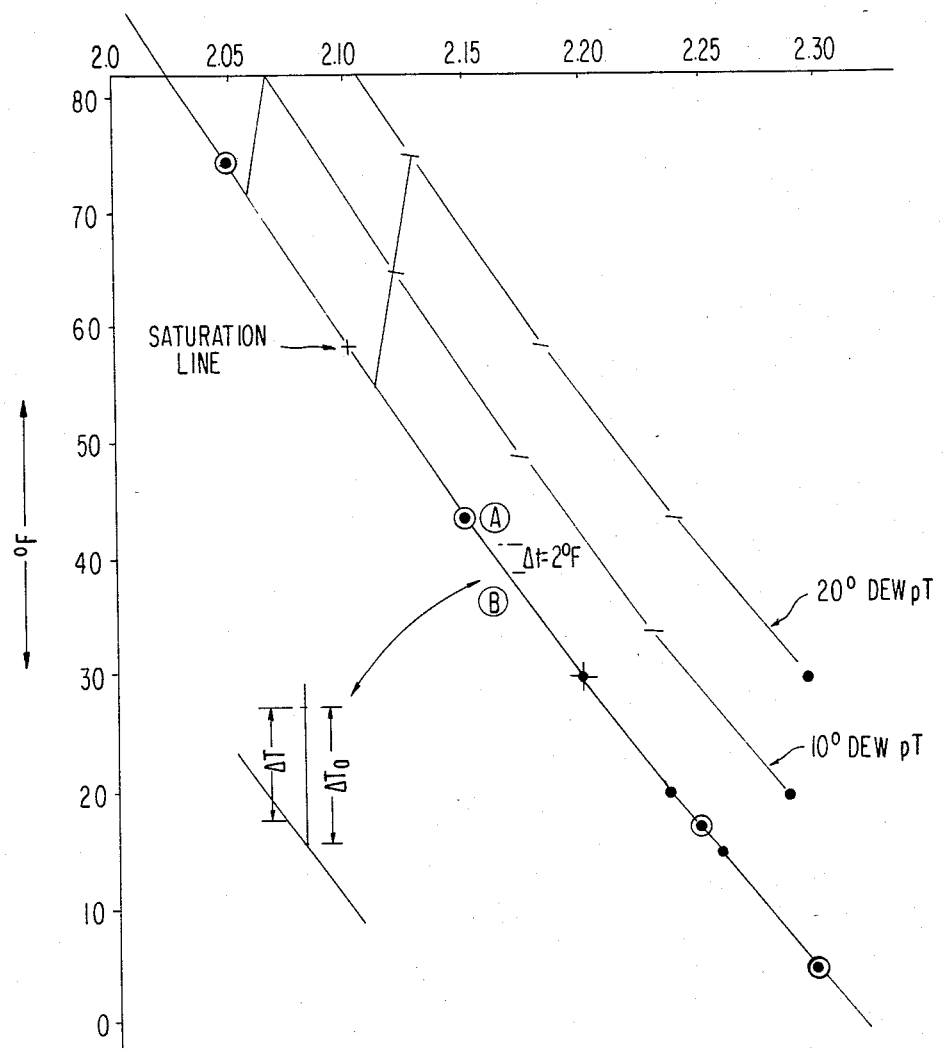
FIG. 4 is a plot of entropy versus temperature for water vapor useful in explaining the theoretical basis of the invention.

FIG. 1 is a cross-section of a first embodiment of the invention; FIG. 2 is a detailed illustration of a portion of FIG. 1 which will be described below. As shown in FIG. 1, a test chamber 10 is contained within a pair of generally parallel end walls 16 and 17 located at opposite ends of a bellows 15. The bellows 15 is arranged in air tight sealing arrangement with the end walls 16 and 17. A valve body 18 is located adjacent the end wall 16 which is rotatable about an axis perpendicular to a plane defined by the end wall 16. The valve body 18 includes conduits 19 and 20 which communicate through holes 41 and 42 in the end wall 16 when the valve body 18 is in the position illustrated in FIG. 1. The conduit 20 allows communication of atmospheric air to the interior of the test chamber 10 when the valve body 18 is in the position shown. Simultaneously, conduit 19 allows communication between the interior of the test chamber 10 via a coacting tube 37 to an aspirating device 21. Accordingly, with the valve body 18 in the position shown, atmospheric air can be communicated to the test chamber 10 and/or the contents of the test chamber 10 can be exhausted via the conduit 19 of the valve body 18 and the cooperating tube 37 through the aspirating device 21.

The end wall 17 is arranged for reciprocating movement provided via an arm 24 coupled to an impulse actuator 25. The movement of the end wall 17 can be constrained by rails 44 and 45, or the equivalent.

The sensing arm 23 of a linear transducer 22 is also coupled to the end wall 17 and the transducer 22 is arranged to output a signal via the conductor pair 31 representative of the position of end wall 17. Such a signal can be used to determine the instantaneous volume of the chamber 10 since the volume of the chamber 10 is determined by the cross-section area of the bellows 15 and the distance between the end walls 16 and 17. Since the cross-section of the bellows 15 is relatively constant, and any change in volume of the test chamber 10 is occasioned only by motion of the end wall 17, the position of the end wall 17 can be used to determine the instantaneous volume of the chamber 10.

Located within the test chamber 10 is a light emitting device, such as the light emitting diode 33 which is energized via the conductor pair 30. Also located within the test chamber 10 is a photo responsive device, for example the photo transistor 34, the voltage across which is output on conductor pair 29. As is schematically illustrated in FIG. 1, there is no direct light path between the light emitting diode 33 and the photo transistor 34, that is light can only be coupled into the photo transistor 34 by being reflected, such as for example by the representative particle 35 which may represent a water droplet and/or ice particle.

Also associated with the test chamber 10 is an ambient temperature sensor 27, which outputs an electrical signal representative of ambient temperature via conductor pair 28. The temperature sensor 27 is protected from direct sunlight by the sun shield 26.

Before describing the operation of the dew point or dew point depression measurement device, reference is made to FIG. 2 which provides one illustration of a region interior of the test chamber 10. As shown in FIG. 2, the light emitting diode 33 is located in non-communicating arrangement with the photo transistor 34. That is, no direct light path exists which will allow light emitted by the light emitting diode 33 to impinge on the photo transistor 34. This effect is produced by selectively locating baffles B. As is referred to above, however, water and/or ice particles, if present within the test chamber 10 may reflect light from the light emitting diode 33 to the photo transistor 34, and this phenomenon is used to detect the presence of water and/or ice particles within the test chamber 10. For calibration and test purposes, however, a second photo transistor 36 is preferably provided within the test chamber 10 which is in communication with the light emitting diode 33. This provides, as will be described more fully hereinafter, ready evidence that the light emitting diode 33 is actually operating.

In operation, assume that the device is about to initiate a cycle of operation. At this point in the cycle, the end wall 17 has been advanced (toward the end wall 16) at a time when the valve body 18 is in position to allow communication to the aspirating fan 21 (which may be energized—or constantly energized). As the end wall 17 advances toward the end wall 16, the contents of the test chamber 10 are exhausted. Motion of the end wall 17 terminates at a reference position, and aspiration continues so that new atmospheric air is brought in via the conduit 20. This aspiration is done slowly so as not to disturb the pressure/temperature relation of the new sample in the chamber 10; and accordingly the sample injected in the chamber 10 will be at or nearly at ambient pressure and temperature. The light emitting diode 33 may now be actuated (or it may be actuated continuously). At the beginning of the cycle, the valve body 18 is rotated so as to move the conduits 19 and 20 out of communication with the test chamber 10. Once this sealing is effected, the impulse actuator 25 is energized to abruptly draw the end wall 17 away from the end wall 16; accordingly, this produces an abrupt increase in the volume of the test chamber 10. Preferably, this abrupt change is sufficient, over the operating range of the instrument, to produce saturated conditions within the test chamber 10, during some point in the travel of the end wall 17. This saturated condition is detected by the photo transistor 34, on detecting light reflected by water and/or ice particles. As the end wall 17 is withdrawn from the end wall 16, linear transducer 22 is noting the instantaneous volume of the chamber 10. The distance between the end walls 16 and 17, at the time a saturated condition is first detected within the chamber 10 is the data which will be used for determination of dew point or dew point depression. The temperature sensor 27 provides ambient temperature indications which will be used as explained below.

The data input, that is the voltage across the conductor pair 29 (which changes abruptly when the chamber 10 becomes saturated), the voltage across the conductor pair 28 (related to ambient temperature) and the voltage on the conductor pair 31 (the output of the transducer 22 which relates to the volume of the chamber 10) is used in a manner to be explained to derive raw dew point or dew point depression data. This data is input to a microprocessor which also establishes the cycle rates (by controlling the impulse actuator 25) as well as energizing the LED 33 and the aspirating device 21. The microprocessor also includes an accurate time reference. Once dew point or dew point depression data is derived, it is stored in association with the time of measurement. The microprocessor thereafter also derives and stores time derivative and time rates of change of dew point and/or of dew point depression data. This allows the microprocessor to output signals not only representing dew point, but also whether the dew point is increasing or decreasing, and the rate of change in degrees per hour. This latter information (magnitude of dew point depression and direction and rate of change) provide positive indicators as to short term future visibility and/or icing probabilities.

A preferred embodiment of the invention is illustrated in cross-section form in FIG. 3. As shown in FIG. 3, the device is housed within a shroud and sun protector 119. Enclosed therein is a base plate 114 to which is mounted a valve 124 and valve actuator 123. The valve 124 includes an inlet/outlet 125 open to the atmosphere, as well as being in communication with the test volume 110, on the other side of the lower plate 114. Located within the test volume 110 is a light emitting diode 33 and a pair of photo transistors 34 and 36, geometrically located as is shown in FIG. 2 (the baffles B of FIG. 2 are included in the test volume 110, but not illustrated in FIG. 3 for convenience). Accordingly, because of the geometrical arrangement between light emitting diode 33, photo transistor 34 and the baffles B, there is no direct ray path between diode 33 and photo transistor 34. Photo transistor 34 can only be illuminated by light reflected from water vapor and/or ice particles. The test volume is defined in part by the lower plate 114, and is furthermore defined by a bellows 112 and upper end plate 126. The upper extremity of the bellows is mounted on plate 126. Plate 126 is supported by end plate support 126A. End plate support 126A has ends 135–137 which cooperate with guide rods 115, 116 extending between the lower plate 114 and an upper plate 117. An arm 128 is pinned to the plate 126A providing for reciprocal movement of the end plate 126 and end plate support 126A and corresponding expansion and contraction of the test volume 110. The arm 128 includes a rack 127 which is in engagement with a gear 129 forming a rack and pinion arrangement. The gear 129 in turn is operated by a motor and gear train 120. Accordingly, by energizing the motor 120 in one direction or the other, the arm 128 can be reciprocated, raising or lowering the plate 126 and providing for corresponding expansion or contraction of the test volume 110. An extension 130 of the arm 128 is fixedly mounted to a linear position transducer 118. Accordingly, output signals from the linear position transducer 118 can be directly related to the volume of the test volume 110. FIG. 3 also illustrates, in association with the apparatus, an electrosensitive temperature indicator such as thermistor 27 with its output conductor pair 28. It should be apparent from the function of the various components that the physical location of the sensor 27 is not crucial so long as it is protected from direct sun exposure and arranged to accurately measure ambient air temperature.

In operation, in a first phase the motor and gear train 120 and gear 129 is operated to compress the bellows 112 with the valve 124 in an open condition. This exhausts air previously present in the test volume 122. In an initial phase of this movement, the valve 124 may be closed, effecting an initial compression to ensure that the temperature of the sample is elevated above freezing for discharge. This ensures that the device is operable even at temperatures slightly below freezing. In any event, at some point in the compression of the bellows 112, the valve 124 is opened to exhaust a previous sample. Thereafter, the motor 120 reverses its direction of rotation, raising the plate 126 tending to expand the test volume 122. At some point in this travel, the valve 124 is closed and the output of the linear position transducer 118 is noted. This provides a reference volume indication, indicating the volume of air within the test volume 122 at ambient pressure and temperature conditions. Although the output of the linear position transducer 118 is noted, the operation of the motor continues and thus the test volume 122 is continually expanded. The output of photo transistor 34 is monitored until such time as it provides an output indicative of incident light. This is taken as indicating the formation of water and/or ice particles, and this initiates another check of the linear position transducer 118 to note the actual volume of the test volume 122 when water vapor and/or ice particles are formed. Recording two positions of the linear position transducer 118, the first when the valve 124 is closed and the second when the photo diode 34 indicates incident light, allows a volume change to be computed which will be useful as described hereinafter.

Insofar as the operating cycle is concerned, the motor 120 is reversed in direction of rotation, causing the arm 128 to descend, and compressing the test volume 122. Since at this time the valve 124 is closed, the sample in the volume is compressed, raising its temperature to freezing or ambient, whichever is greater. Thereafter, the valve 124 is opened, ventilating the test volume 122 to atmosphere.

Dew point is by definition the temperature to which air must be cooled to become saturated along a constant pressure contour. To implement this requirement, the expansion and compression of the test volume 110 is effected quickly, and the materials of the components shown in FIG. 3 are selected to have good temperature isolating properties, all in an effort to ensure that the transitions caused by compression and expansion are adiabatic. Adiabatic changes are constant entropy by definition. FIG. 4 illustrates a region of the temperature-entropy diagram for water vapor. Lines of constant dew point, for 0°, 10° and 20° are also shown. If we assume that the atmospheric sample starts at point A, and an adiabatic change is made (constant entropy) to saturation, then our end point will be point B (a constant entropy line from point A to the saturation line). The inset in FIG. 4 is the region between points A and B, greatly magnified for purposes of this description. The formula for adiabatic changes are:

$$P2/P1 = (V1/V2)^k = (T2/T1)^{k/(k-1)},$$

where P, V and T refer respectively to pressure, volume and temperature and the indices 1 and 2 refer to conditions at points A and B, respectively.

Raising this equation to the power 1/k gives:

$$V2/V1 = (P1/P2)^{1/k} = (T1/T2)^{1/(k-1)}.$$

Raising all terms to the power (k−1) gives:

$$T2/T2 = (P2/P1)^{(k-1)/k} = (V1/V2)^{(k-1)}.$$

However, from FIG. 4 we note that T2=T1+ΔTa. At the dew point, or in the vicinity of the dew point, we can approximate ΔTa/1.06895=ΔT. This constant, 1.06895, varies slightly over the ambient range of 0° F. to 120° F., and is easily interpolated by the microprocessor (to be described hereinafter). Thus, knowing the temperature change ΔTa, we can determine the dew point depression ΔT. From the equation last written, ΔTa can be derived by knowing the starting and final volumes V1 and V2. This measurement is controlled by the accuracy of the linear position transducer 118, and this accuracy is increasingly good at small displacement changes. In other words, our accuracy of measurement of dew point depression is more and more accurate at or near the dew point, which is exactly the characteristic missing from the prior art.

As described above, the temperature sensor 27 is used to sense ambient temperature. It is theoretically possible to locate a temperature responsive device within the test volume 122, itself. An advantage is directly measuring the parameter ΔTa; conceivably this could make the change of volume measurement unnecessary. However, because of the desire to make the volume change occur rapidly (to maintain nearly adiabatic conditions), a temperature sensor sensitive enough to respond in that short period of time would also be mechanically fragile. Slowing the volume change, in an effort to use a more mechanically robust temperature sensor, would make the expansion non-adiabatic due to heat transfer.

Both the embodiments of FIGS. 1 and 3 use a mechanical actuator and/or rack and pinion to provide the necessary mechanical motion for the expansion operation and a linear position sensor (22 or 118) to enable a change in volume to be calculated. However, this combination of elements is not essential to the invention. For example, a digital stepper motor could replace the actuator 25 and/or motor gear train 120. Digital stepper motors have a characteristic that directly relates change in position or angular motion of an output shaft (which, through a gear and rack and pinion, can be related to a change in position of the end plate 126, and hence the volume of the test chamber 122) to a number of input pulses. This characteristic makes the linear position transducer 118 unnecessary. Using the digital stepper motor, the microprocessor pulses the motor at an appropriate rate to provide the required rapid change in volume, and merely notes the number of pulses required before the photo transistor 34 produces an output. The number of input pulses to the digital stepper motor can be directly related to a volume change of the test chamber 122.

Figure 5:
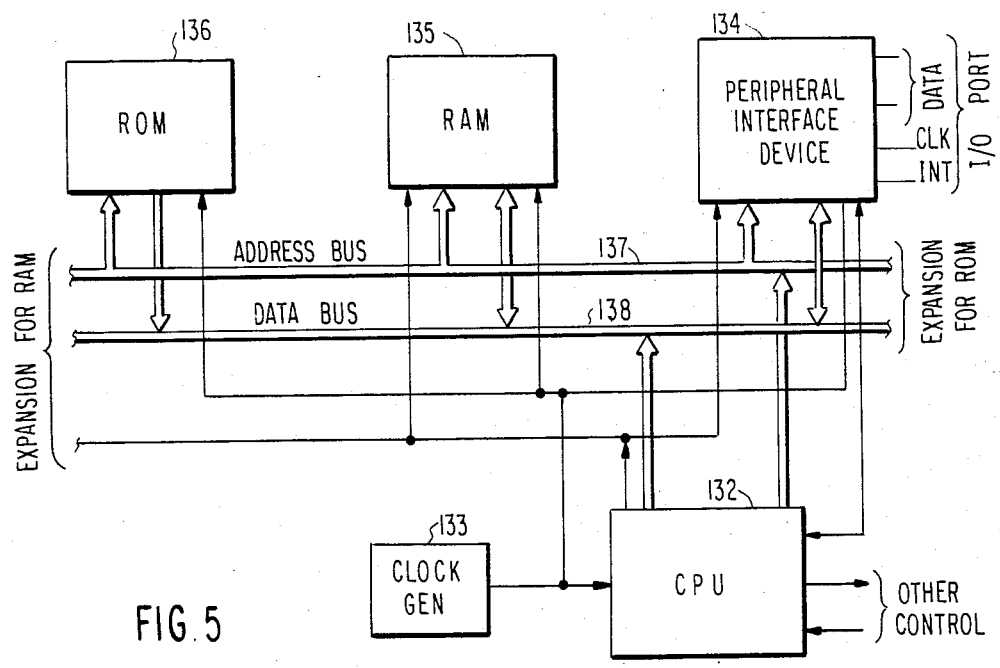
FIG. 5 is a block diagram of the device control which, when interfaced with the components shown in either of FIGS. 1 and 2 or 3, provides for ready dew point or dew point depression measurement.

FIG. 5 delineates certain major features of a microprocessor used to control the cycle of operation, record the data and compute the desired dew point and trend analysis. These are:
Central Processor Unit (CPU): 132
Clock Generator: 133
I/O Port: 134
Read Only Memory (ROM): 136
Random Access Memory (RAM): 135

The CPU 132 is the heart of the microprocessor and performs a repertoire of logic functions upon binary input data. This data typically is in units or blocks 8-bits wide and commonly referred to as bytes. The instructions and data needed by the CPU are requested by the address bus 137. The returned information comes via the data bus 138 and can result from ROM 136, RAM 135 or peripheral interface device 134. It is possible under CPU control for data to flow from 134 to 135 via 138 or from 135 to 134 via 138. This is a frequent occurrence when data requires additional processing.

The most usual situation is that the algorithm or program is stored in ROM 136, since it does not change. Measured data and dynamically changing values are stored in RAM 135. Sampled input is via 134, as are outputted values via 134 to the I/O port.

The clock generator 133 is crystal controlled so that accurate time reference is always available. The data through the I/O port is digital and external devices such as the linear transducer 118 may require an A/D (analog to digital) converter to assure binary digital data. Similarly, motor 120 may require conversion to analog values via a D/A. Typically, these digital interfaces are 3-state so they may be directly paralleled and read into or out of as the CPU 132 requires.

The CPU 132 under ROM 136 control can perform data manipulation as well as add, subtract, multiply, divide or any combination thereof in any sequence.

In view of the foregoing description, the manner in which the CPU 132 can acquire data, temporarily store it, and manipulate it to provide intermediate results should be apparent. However, through the peripheral interface device 134, the CPU 132 can also manifest commands to attached devices. More particularly, it can operate the valve actuator 123 via commands coupled over the conductor 201, it can actuate the motor and gear train 129 via commands coupled over the conductor 203. In addition, once final results have been determined, it can pass those results to a voice synthesizer and simultaneously enable radio equipment for communicating the computed information to any receiver tuned to the carrier frequency of the radio.

Figure 6:
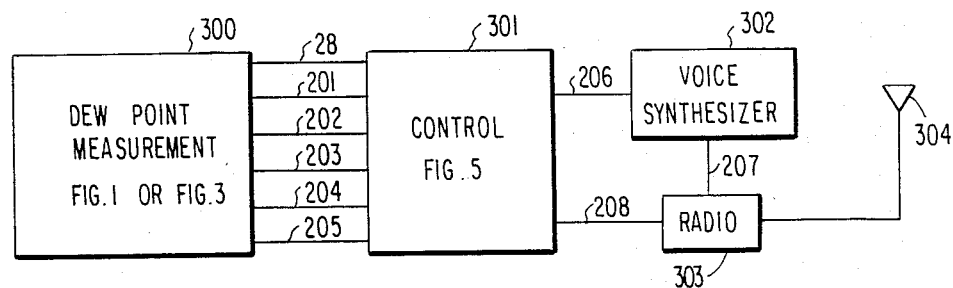
FIG. 6 is a block diagram interrelating device, device control, voice synthesizer and radio.

Accordingly, FIG. 6 is a block diagram illustrating the cooperation between a dew point measuring device 300 (which can take the form shown in FIG. 1 or FIG. 3, for example), a control device 301 (which can be that illustrated in FIG. 5), and a voice synthesizer 302 and a radio 303.

As will be described in more detail below, the control device 301 controls the dew point measuring device 300 so as to cycle the device 300; in the course of this cycling operation, the control device 301 acquires data from which dew point depression can be determined. In addition to determining dew point depression, the control device 301 also stores, as a function of time, previously computed dew point. Accordingly, in addition to determining present dew point, the control device 301 can also develop through a time trend analysis, short term predictions for future dew point depression. The control device 301 couples the computed present point dew point depression and short term predictions to a voice synthesizer 302. The information will typically be communicated via a digital code, the voice synthesizer 302 responds to the digital code and produces an audio signal (synthetic speech) which enunciates the information communicated in digital form. For example, this synthetic speech can be a message "present dew point depression: 3°, predicted dew point depression in 30 minutes: 1°".

The output of the voice synthesizer is coupled via a conductor 207 to the modulating input of a radio 303. The analog signal on the conductor 207 is used to modulate the carrier frequency of the radio 303, and the resulting modulated information is radiated via an antenna 304. The radio 303 itself may be controlled (enabled/disabled) by signals from the peripheral interface device over a conductor 208. The radio 303 is indicated as a transmitter. It is possible for it to be a transceiver, i.e. a transmitter and receiver. In such a sequence, the pilot desiring the dew point information will operate his transmitter in some unique manner recognizable by the receiver of 303. A signal will pass via 208 to the control 301, which in turn, via 206 and 208, initiates a broadcast of dew point information, then returns to listening via the receiver of 303 for another request. The uniquely recognizable signal from the pilot could be keying the carrier a certain number of times, indicating a particular tone, etc. if the receiver in 303 is not interrogated within a certain period, say 5 minutes, the transmitter of 303 can transmit its message automatically.

Referring again to the control device 301, the ROM 136 stored program provides for cyclical operation of the dew point measurement device 300, including opening and closing the valve 125 and operating the motor and gear train 129 in a manner described above. In the course of this cyclical operation, the same program allows the peripheral interface device 134 to couple signals from selected input at appropriate times. For example, a temperature dependent signal via the conductor 28 is continuously available, and checked at appropriate times to derive a present ambient temperature parameter which will be used in computing dew point.

After the test chamber 122 has been filled under atmospheric conditions, and the valve 125 is closed, the signal on the conductor 202 (from the position transducer 118) is read to define an initial volume parameter (V1). In accordance with the cycle of operation, the motor and gear train 129 is enabled to expand the test volume 122. At this time, the output conductor 205 (coupled to the photo detector 34) is monitored, and when a signal is detected indicating the presence of reflected light, the signal on the conductor 202 is again captured. This signal corresponds to a second volume measurement giving the parameter V2. Knowing T1, V1 and V2, T2 can be computed using the above-described equations. From T1 and T2, we can compute $\Delta Ta$ and from that parameter, the dew point depression. In additional to being a final computed result, dew point depression is also stored along with the time of the measurement, derived from the clock generator 133. From this present dew point computation, along with previously stored dew point depression and time of measurement information, a rate or trend of dew point change as a function of time can also be determined. This rate could be applied to predict dew point at a predetermined time in the future (for example 30 minutes) or the rate could be used to predict the quantity of time which must pass before the dew point depression reached zero (if ever at the present rate). There are a variety of well known extrapolation algorithms which can be applied to this purpose.

From the foregoing, it should be apparent that the invention provides a device satisfying the objects in that dew point depression can be accurate measured over the particular ranges of interest, i.e. high humidity, low temperature, and in addition to accurately computing dew point depression under the conditions of interest, trend data can be developed so as to predict short term future dew point depression.

I claim:

1. A dew point depression measuring device comprising:
   a test chamber with conrollable volume,
   first means for introducing air into said chamber at near ambient temperature and pressure conditions,
   second means for opening and closing said test chamber to ambient atmospheric conditions,
   third means for abruptly expanding said test chmaber in volume after said test chamber is sealed from said atmosphere by said second means,
   fourth means for detecting formation of ice or water particles in the test chamber,
   and a microprocessor including:
   fifth means for recording test chamber volume at the time said fourth means detects said formation of ice or water particles, and
   sixth means for computing dew point based on ambient temperature and said recorded test chamber volume,
   whereby said test chamber is controlled in volume, and said second, third and fourth means are coordinated in operation by said microprocessor.

2. The device of claim 1 wherein said sixth means includes storage means for storing historical dew point depression data and trend analysis means for predicting future dew point depression.

3. The device of claim 1 in which said fifth means records test chamber volume just prior to expansion of test chamber volume by said third means and wherein said sixth means determines dew point depression from a ratio of said recorded volumes.

4. The device of claim 1 wherein said fourth means includes a source of optical energy, an optical energy detector and means for preventing any straight line light path from said source to said detector.

5. The device of claim 4 in which said fourth means includes a second optical energy detector and means for mounting said second optical energy detector to image said source.

6. The device of claim 1 or 2 in which said sixth means includes means for outputting computed results, and which further includes:
   voice synthesizer means responsive to said computed results of said sixth means for a vocalized output, and
   a radio responsive to said vocalized output of said voice synthesizer means.

7. The device of claim 1 in which said third means compresses test chamber volume following said abruptly expanding of the test chamber volume.

8. A method of accurately measuring dew point depression under high relative humidity conditions comprising a microprocessor to coordinate the steps of:
   (a) providing a valved test chamber of controllable volume,
   (b) introducing air to the test chamber at nearly ambient temperature and pressure conditions,
   (c) sealing the chamber,
   (d) abruptly increasing the volume of said chamber,
   (e) detecting the formation of ice or water particles,
   (f) recording the volume of said chamber at which said water or ice particles are formed, and
   (g) calculating, from said recorded volume of said chamber, the dew point depression.

9. The method of claim 8 which includes steps, subsequent to step (e) of:
   (h) decreasing the volume of said chamber to raise its temperature to ambient, or at least 0° C., and then
   (j) opening said chamber to atmospheric condition.

10. The method of claim 8 in which said step (e) includes:
    (i) providing a light source in said chamber,
    (ii) providing a light detector in said chamber with a field of view excluding said light source, and
    (iii) sensing light reflected into said light detector to signal formation of ice or water particles.

11. The method of claim 8 which includes a step of sensing ambient temperature and in which said steps (e)–(g) determine dew point depression by determining a ratio of V1 and V2 where V1 is chamber volume at ambient conditions, and V2 is chamber volume on formation of ice or water particles.

12. The method of claim 9 which includes the further step (k) of recording dew point depression and a current time quantity.

13. The method of claim 12 in which said steps (a)–(k) are repeatedly performed in a cyclical fashion.

14. The method of claim 13 which includes a further step of predicting future dew point depression by performing a time trend analysis of change in dew point depression as a function of time.

15. The method of any one of claims 8–14 which includes the further steps of:
    synthesizing a voice message including said determined dew point depression, and
    broadcasting said synthesized voice message.

* * * * *